United States Patent [19]

Cleveland et al.

[11] Patent Number: 4,767,704

[45] Date of Patent: Aug. 30, 1988

[54] PROTEIN-FREE CULTURE MEDIUM

[75] Inventors: William L. Cleveland, New York; Bernard F. Erlanger, Whitestone, both of N.Y.

[73] Assignee: Columbia University in the City of New York, New York, N.Y.

[21] Appl. No.: 539,954

[22] Filed: Oct. 7, 1983

[51] Int. Cl.$^4$ .................. C12P 21/00; C12N 5/00; C12N 5/02; C12R 1/91

[52] U.S. Cl. .................. 435/68; 435/240.25; 435/240.27; 435/240.3; 435/240.31; 435/948

[58] Field of Search ............. 435/240, 241, 68, 948, 435/240.25, 240.27, 240.3, 240.31

[56] References Cited

PUBLICATIONS

Reinert, J. and M. M. Yeoman, *Plant Cell and Tissue Culture*, NY, Springer-Verlag, 1982, pp. 77–79.
McKeehan, W. L., K. A. McKeehan, S. L. Hammond and R. G. Ham, *In Vitro*, 13(7), 399–416, 1977.
Chang et al., "Production of Monoclonal Antibodies in Serum Free Medium", *J. of Immunological Methods*, vol. 39, pp. 369–375, 1980.
Hamilton, Clonal Growth of Chinese Hamster Cell Lines", 1977, *In Vitro*, vol. 13, No. 7, pp. 537–547.
Cleveland et al., *J. of Immunological Methods*, vol. 56, pp. 221–234, 1983.
Mosier, "Primary In Vitro Antibody Responses", 1981, *J. of Immunology*, vol. 127, No. 4, pp. 1490–1493.
Schroeder et al., *Arch. Environ. Health*; vol. 23, Aug. 1971, pp. 102–106.
Titanium, *World Health Organization*, Geneva, 1982, pp. 12–49.
James N. Ihle et al., *Journal of Immunology*, 126, Jun. 1981, pp. 2184–2189.
Kearney et al., *Journal of Immunology*, 123, Oct. 1979, pp. 1548–1550.
Yelton et al., *Hybridoma*, 1, 1981, pp. 5–11.
Laskov and Scharff, *J. Exp. Med.*, 131, 1970, pp. 515–541.
Benjamin et al., *Proc. Natl. Acad. Sci. USA*, 79, 1982, pp. 5379–5383.
Kincade et al., *J. of Immunological Methods*, 42, 1981, pp. 17–24.
Marshak-Rothstein et al., *J. of Immunology*, 122, 1979, pp. 2491–2497.

*Primary Examiner*—Thomas G. Wiseman
*Assistant Examiner*—Veronica Dutch
*Attorney, Agent, or Firm*—Oblon, Fisher, Spivak, McClelland & Maier

[57] ABSTRACT

A trace element mixture suitable for use in a protein-free tissue culture medium, which comprises water-soluble compounds selected from acids, bases, and salts containing copper, iron, zinc, manganese, silicon, molybdenum, vanadium, nickel, tin, aluminum, silver, barium, bromine, cadmium, cobalt, chromium, fluorine, germanium, iodine, rubidium, zirconium, or selenium, the compounds being devoid of any additional metals other than those present as positive ions selected from groups IA and IIA of the periodic table of elements, wherein the compounds produce a solution containing specified minimum concentrations of the listed elements when dissolved in an amount of water sufficient to produce a concentration for one of the elements equal to the corresponding minimum concentration of the one element while maintaining each remaining element at a concentration equal to or greater than the minimum concentration for the remaining element is disclosed along with cell culture media containing these trace elements and methods of culturing cells using these media.

23 Claims, 2 Drawing Sheets

PROTEIN-FREE CULTURE MEDIUM

The investigations leading to the present invention were supported in part by National Institutes of Health grants AI-06860 and AI-17949.

BACKGROUND OF THE INVENTION

1. Field of the Invention

The present invention relates to a protein-free culture medium useful for the routine large-scale production of monoclonal antibodies and other cell-produced substances of biological and clinical importance.

2. Description of the Prior Art

The use of antibodies in all areas of medicine and biology has expanded rapidly since the 1975 publication by Kohler and Milstein of their technique which allows the production of monoclonal antibodies of desired specificity. Previously used conventional antisera, sometimes known as polyclonal antibodies, were reactive with many determinants and thus were of limited use in identifying or targeting specific determinants. In contrast, monoclonal antibodies possess homogeneity, thus greatly facilitating the standardization and reproducibility of immunochemical procedures. However, it is necessary to obtain the antibodies in a highly purified state if many of their desirable properties are to be fully realized, especially if they are to be used therapeutically.

Currently, monoclonal antibodies are generally produced by growing cells in the presence of serum, either in vivo by ascites tumors or by cultivation in vitro in a medium supplemented with serum, preferably antibody-free serum. Since both ascites fluid and serum-supplemented culture media are highly complex mixtures of proteins and other molecules, and since the monoclonal antibodies being produced are themselves proteins, purification of the antibodies from the mixture is difficult and time-consuming. Furthermore, so-called antibody-free serum such as fetal calf serum (which is, in fact, never completely free of antibody) is extremely expensive and is a significant factor in determining the overall cost of the media.

Accordingly, previously investigators have attempted to grow hybridoma lines in media free of serum. However, other proteins and macromolecules were always added to these media in order to allow long-term growth of the hybridoma lines. For example, serum-free media supplemented with serum proteins such as transferrin and insulin (Chang et al, *J. Immunol. Methods*, 39: 369 (1980)) or transferrin and insulin plus albumin containing liposomes (Andersson and Melchers, *Curr. Top. Microbiol. Immunol.*, 81: 130 (1978)) have been used. Another medium used the dialyzable fraction of serum for small-scale cultivation with a two-chambered Marbrook vessel (Klinman and McKearn, *J. Immunol. Methods*, 42: 1 (1981)). Serum proteins were avoided in still another medium, but cultivation was restricted to 24-48 hours because of cell death (Galfre and Milstein, *Methods in Enzymology*, Vol. 73B, eds. Colowick and Kaplan, Academic Press, New York, page 1, 1981). However, none of these methods allows for the routine large-scale production of monoclonal antibodies in a protein-free culture medium, and such a production process and culture medium are still needed.

Several non-hybridoma mammalian cell types have been grown in either serum-free or protein-free media. For example, murine B lymphocytes have been shown to survive and grow in a medium containing insulin, transferrin and progesterone instead of serum (Mosier, *J. Immunol.*, 127, 1490-1493 (1981)). A trace element mixture was used to replace serum in producing the protein-free medium MCDB 301, which is capable of supporting the growth of Chinese hamster ovary cell lines (Hamilton and Ham, *In Vitro*, 13, 537-549 (1977)). Such media, however, have not been applied to growing hybridoma cell lines or cells used for preparative production of biologically and clinically useful substances.

SUMMARY OF THE INVENTION

Accordingly, it is an object of the present invention to provide a protein-free culture medium suitable for the long-term growth of antibody-producing hybridoma cells and other cells which produce biologically or clinically useful substances.

This and other objects of the invention as will hereinafter become more readily apparent have been accomplished by providing a trace element mixture suitable for use with a protein-free tissue culture medium whereby the necessity of providing serum or proteins is avoided. The trace element mixture consists essentially of water-soluble compounds selected from acids, bases, and salts containing copper, iron, zinc, manganese, silicon, molybdenum, vanadium, nickel, tin, aluminum, silver, barium, bromine, cadmium, cobalt, chromium, fluorine, germanium, iodine, rubidium, zirconium, or selenium, said compounds being devoid of any additional metals other than those present as positive ions selected from groups IA and IIA of the periodic Table of elements, wherein said compounds produce a nontoxic solution containing

| Elements | Minimum Concentrations (mg/L) |
|---|---|
| copper | $3.1 \times 10^{-10}$ |
| iron | $8.4 \times 10^{-8}$ |
| zinc | $9.9 \times 10^{-8}$ |
| manganese | $2.8 \times 10^{-11}$ |
| silicon | $7.0 \times 10^{-9}$ |
| molybdenum | $4.8 \times 10^{-11}$ |
| vanadium | $1.3 \times 10^{-10}$ |
| nickel | $1.4 \times 10^{-11}$ |
| tin | $3.1 \times 10^{-11}$ |
| aluminum | $1.3 \times 10^{-10}$ |
| silver | $1.1 \times 10^{-10}$ |
| barium | $1.4 \times 10^{-9}$ |
| bromine | $4.0 \times 10^{-11}$ |
| cadmium | $1.1 \times 10^{-9}$ |
| cobalt | $6.0 \times 10^{-10}$ |
| chromium | $5.3 \times 10^{-11}$ |
| fluorine | $2.3 \times 10^{-9}$ |
| germanium | $3.7 \times 10^{-10}$ |
| iodine | $4.1 \times 10^{-11}$ |
| rubidium | $8.5 \times 10^{-10}$ |
| zirconium | $9.0 \times 10^{-10}$ |
| selenium | $2.6 \times 10^{-9}$ | when dissolved in an amount of water sufficient to produce a concentration for one of said elements equal to the corresponding minimum concentration of said one element while maintaining each remaining element at a concentration equal to or greater than the minimum concentration for said remaining element.

Tissue culture media prepared in a manner so as to contain these concentrations of trace elements are also provided by this invention as is a method of growing cells in such media, particularly hybridoma cells and other cells that produce biologically and/or clinically useful substances, such as cytokines.

BRIEF DESCRIPTION OF THE DRAWINGS

A more complete appreciation of the invention and many of the attendant advantages thereof will be readily obtained by reference to the following detailed description when considered in connection with the accompanying drawings, wherein.

DESCRIPTION OF THE PREFERRED EMBODIMENTS

Figure 1A:
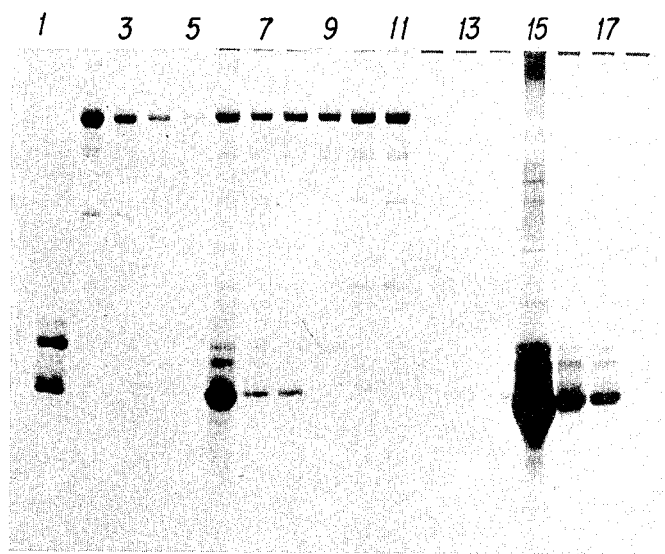
FIG. 1 shows a sodium dodecylsulfatepolyacrylamide gel electrophoresis (SDS-PAGE) analysis of antibody in serum-supplemented and serum-free tissue culture media in comparison to a protein-free medium of the invention.

The present invention arose with the discovery that protein supplements could be eliminated from media used to grow monoclonal antibody-producing hybridoma cell lines by replacing the protein supplements in an otherwise rich, balanced basal media with a mixture of trace elements. It has been demonstrated that this mixture of trace elements can be used to replace serum components in media known to be useful for growing hybridoma cell lines and other animal cells. Using the formulations of the invention, it is possible to eliminate liposomes and all protein supplements, making the medium totally synthetic and chemically defined within the limits imposed by the purities of the substances used.

The elimination of albumin, transferrin, and insulin is an important advance in hybridoma media since these substances are expensive and are potential sources of artifacts, for example, in the use of monoclonal antibodies to determine cell surface antigens. For example, it has recently become popular to use fluorescent avidin and biotinylated antibodies for immunofluorescence detection of cell surface antigens. Biotinylation of monoclonal antibody preparations contaminated with insulin or transferrin will produce biotinylated insulin and biotinylated transferrin. Since subpopulations of lymphocytes have been shown to have large numbers of high affinity receptors for transferrin and also high affinity receptor for insulin, spurious staining could easily result. Moreover, commercially available albumin and transferrin are far from being pure substances and may contain traces of immunoglobulins, which would be difficult to separate from the desired monoclonal antibodies. Furthermore, the elimination of proteins facilitates the purification of monoclonal antibodies for use as therapeutic agents that can be given to humans, since vigorous standards of purity can more easily be met.

Although various protein-free media for the growth of bacteria exist, no protein-free medium capable of providing the long-term growth requirements of mammalian myeloma and hybridoma cell lines existed prior to the present invention. By long-term is meant more than 10 days and preferably more than one month with fresh medium supplied as necessary. A protein-free medium of the invention has been demonstrated to support the growth of a mouse hybridoma cell line for more than 77 days and cultivation for periods of time greater than 5 months has been demonstrated for a mouse-rat hybridoma cell line, 10 months for Ehrlich ascites tumor cells, and two months for Friend leukemia cells.

Any protein-free basal medium which will support the long term growth of a hybridoma cell line when supplemented with 5% fetal calf serum or similar serum or protein components can be supplemented with the trace elements of the invention instead of the serum or protein components which are normally used for that cell line. Basal media useful for the growth of various types of cell lines when supplemented with serum or protein sources are well-known, as exemplified by the American Type Culture Collection Catalogue of Strains II, Third edition, 1981, pages 29–185, which are herein incorporated by reference. For example, Ham's F10 medium, which is often supplemented with fetal bovine serum, is supplemented instead with the trace element mixture of this invention to produce a protein-free medium of the invention. Preferred are basal media which do not contain any protein or serum components, although a known basal medium may be modified by removing protein and serum components and thereafter used with the trace elements of this invention. Preferred media include Medium 199, CMRL 1066, CMRL 1415, CMRL 1066, CMRL 1415, Eagle's Basal Medium, Eagle's Minimum Essential Medium, Dulbecco's Modification of Eagle's Medium, NCTC 109, NCTC 135, Puck's N15, Puck's N16, Ham's F10, Ham's F12, Ham's F12M, Ham's F12K, MCD 101, MCDB 102, MCDB 103, MCDB 104, Waymoth's MB 752/1, McCoy's 5A, RPMI 1603, RPMI 1634, RPMI 1640, Leibovitz's L15, and ATCC-CRCM 30. Of these, Ham's F10, Ham's F12, Ham's F12M, Ham's F12K, MCD 101, MCDB 102, MCDB 103, MCDB 104, Waymoth's MB 752/1, McCoy's 5A, RPMI 1603, RPMI 1634, RPMI 1640, Leibovitz's L15, and ATCC-CRCM 30 are most preferred. Also preferred are media prepared by mixing two or more known basal media. For example, a particularly preferred basal medium of the present invention comprises a 1:1 mixture of IMDM and Ham's F12. IMDM is Iscove's Modification of Dulbecco's Medium (previously listed) and is described in Iscove and Melchers, *J. Exp. Med.*, 147, 423 (1978), which is herein incorporated by reference. This listing of preferred basal media is not intended to limit the present invention but is exemplary thereof.

A basal medium suitable for use with this invention will contain all the essential carbon sources which cannot be synthesized by the cell line being cultivated. These carbon sources include but are not limited to essential amino acids and lipids. These will naturally vary from cell type to cell type being cultivated and are well-known to those skilled in the art. If desired, the basal medium may be made suitable for general use by including all naturally occurring amino acids and by including other common biological reagents such as putrescine, hypoxanthine, linoleic acid, lipoic acid, α-thioglycerol (or a different reducing agent), and thymidine. Other essential ingredients for growth may be included as needed in preparing a basal medium for use with the present invention. Typical examples include vitamins, such as biotin, pantothenate, choline, folic acid, inositol, nicotinamide, pyridoxal, pyridoxine, riboflavin, thiamine, and vitamin $B_{12}$. Other reagents which may be included in the basal medium include an energy source as a saccharide or polysaccharide. Of these, glucose is commonly used and is preferred. Pyruvate may be also be added.

The basal medium will also normally contain various inorganic ions other than those which are being added as the trace elements. For the purposes of this invention, elements which normally would be present at concentrations greater than 1 mg/L in the basal medium are not considered to be trace elements. These include calcium, potassium, magnesium, sodium, chloride phosphate, and bicarbonate ions. Although the concentration of these ions may vary considerably, as is well known in the art, the total ionic strength of the media will be controlled to a value near that which is typically present in the organism in which the cell line is normally found (i.e., to a physiological inonic strength).

Basal media for use with this invention may contain additional components normally present in cell culture media, such as buffering agents and pH indicators. Typically, a basal medium will have a pH in the range of 6.5–8.2 preferably 7.0–7.7, and most preferably 7.2–7.5. Phenol red is a typical indicator added to aid in the control of pH. Other ingredients that may be added include antibiotics, such as penicillin and streptomycin, and hormones, such as progesterone.

In its broadest aspect, the present invention involves a trace element mixture used to replace serum and protein components in tissue culture media. The components of the trace element mixture can be added individually to a protein-free basal medium or a ready-to-use trace element mixture containing all of the components can be prepared which is then mixed with (if in liquid form) or dissolved in (if in solid form) a protein-free basal medium.

The individual components of the trace element mixture are added to the basal medium in the form of water-soluble compounds selected from acids, bases, and salts containing the essential trace elements. The compounds used to form the trace element mixture should be devoid of measurable contamination by any additional metal (such as Ti, Pb, As or Hg) other than those stated as essential or those present as positive ions selected from groups IA and IIA of the periodic table of elements. However, minute amounts of other elements in a growth medium resulting from impurities in the compounds used to produce the medium but which cannot readily be eliminated by current techniques do not remove a medium from the scope of this invention. Ions from groups IA and IIA are preferably limited to $Na^+$, $Mg^{2+}$, $K^+$, $Ca^{2+}$, and $Ba^{2+}$. Likewise, media subject to this limitation are also preferred, and media which contain no metals other than those recited in this application as positively contributing to a growth medium are especially preferred.

The essential trace elements of the present invention are copper, iron, zinc, manganese, silicon, molybdenum, vanadium, nickel, tin, aluminum, silver, barium, bromine, cadmium, cobalt, chromium, fluorine, germanium, iodine, rubidium, zirconium, and selenium. A compound is water-soluble if it will dissolve in pure water at 20° C. to the extent stated in this specification for that element. These elements are present when dissolved in water in the form of ions. The ionic sources of these elements are not limited other than by toxicity. Generally, the metals will be provided as positively charged ions, the halogens as monovalent negative ions, and the remaining non-metallic elements as negatively charged oxy ions. However, metals may also be provided as negatively charged oxy ions, for example, $MoO_4^{2-}$ and $VO_3^-$. Preferred positive counter ions are ammonium, sodium, and potassium. Preferred negative counter ions are chloride and nitrate, with nitrate being especially preferred. Non-toxic counter ions should be used at all times. By non-toxic is meant throughout this application that growth of the cell type being cultivated is not retarded by the material in question at the concentration stated compared to the growth rate in a medium otherwise identical but not containing the material in question.

Ions which may exist in more than one oxidation state may be provided in any convenient oxidation state. Nevertheless, certain ionic forms are g,17 preferred. These are $Cu^{2+}$, $Fe^{2+}$ and $Fe^{3+}$, $Zn^{2+}$, $Mn^{2+}$, $SiO_3^{2-}$, $MoO_4^{2-}$, $VO_3^-$, $Ni^{2+}$, $Sn^{2+}$, $Al^{3+}$, $Ag^+$, $Ba^{2+}$, $Br^-$, $Cd^{2+}$, $Co^{2+}$, $Cr^{6+}$, $F^-$, $Ge^{4-}$, $I^-$, $Rb^+$, $Zr^{4+}$, and $SeO_3^{2-}$.

Suitable water-soluble compounds containing the essential trace elements for use with this invention include aluminum nitrate, aluminum oleate, aluminum sulfate, ammonium bromide, ammonium cadmium chloride, ammonium chromate, ammonium cobalt orthophosphate, ammonium copper (II) iodide, ammonium iodide, ammonium iron (II) selenate, ammonium permanganate, ammonium manganese phosphate, ammonium molybdate, ammonium nickel chloride, ammonium oxalatoferrate (III), ammonium phosphomolybdate, ammonium selenate, ammonium selenide, ammonium metavanate, ammonium vanadium sulfate, ammonium zinc sulfate, barium fluorosilicate, barium gluconate, barium iodide, barium manganate, barium molybdate, barium nitrate, barium propionate, hydrogen bromide, cadmium acetate, cadmium bromide, cadmium hydroxide, cadmium nitrate, cadmium selenate, cadmium metasilicate, calcium chromate, calcium iodide, calcium permanganate, calcium selenide, chromium (III) nitrate, cobalt (II) acetate, cobalt (II) bromide, cobalt (III) chloride, cobalt (II) iodide, cobalt (II) selenate, hexammine cobalt (II) bromide, copper (II) acetate, hexammine copper (II) chloride, copper (II) chloride, copper (I) salicylate, hydrogen fluoride, germanium difluoride, germanium dioxide, germanium sulfide, hydrogen iodide, iodic acid, iron (II) acetate, iron (III) bromide, iron (II) chloride, iron (III) chloride, iron (II) oxalate, lithium molybdate, manganese (II) acetate, manganese dibromide, permanganic acid, molybdenum pentachloride, molybdenum hydroxide, molybdenum pentoxide, nickel chloride, nickel fluoride, nickel nitrate, hexamminenickel (II) nitrate, potassium bromide, potassium cadmium iodide, potassium chromate, potassium dichromate, potassium copper (II) sulfate, potassium cyanoargenate (I), potassium fluoride, potassium fluorozirconate, potassium metagermanate, potassium permanganate, potassium molybdate, potassium metasilicate, rubidium acetate, rubidium bromide, rubidium nitrate, rubidium trioxide, selenic acid, selenium tetrachloride, selenium trioxide, selenious acid, silver acetate, silver nitrate, sodium metaaluminate, sodium bromide, sodium chromate, sodium iron (III) oxalate, sodium manganate, sodium silicate, sodium metasilicate, sodium hydroxostannate, tin (IV) fluoride, tin (II) chloride, tin (II) nitrate, tin (II) sulfate, vanadium tribromide, vanadium pentoxide, zinc acetate, zinc bromide, zinc sulfate, zirconium tetrachloride, zirconium hydroxide, and zirconium sulfate. Many other soluble and slightly soluble compounds capable of furnishing the elements required by the present invention in water soluble form are also known.

The minimum amount of each essential element is shown in the following table, which also gives a preferred range and a most preferred range for each element. These are the concentrations for the elements listed, not for the compound or ionic source of the element (e.g., for Se, not for $Na_2SeO_3$ or $SeO_3{}^{2-}$). The amount of compound needed to produce these concentrations can be determined by a simple mathematical calculation from the known atomic weight of the element and the formula weight of the compound containing the element. In all cases, the maximum concentration of each individual element is limited by solubility and by toxicity. This toxicity will vary from cell line to cell line and can easily be determined by simple experimentation if not already known. Toxicity is compared to a basal medium containing 5% fetal calf serum instead of the trace element in question.

known media contain some, but not all, of the essential trace elements of this invention. These media can be converted into media of the invention either by adding the complete trace element mixture (providing that concentration or toxicity limits are not thereby reached) or by adding individual trace elements to produce a medium containing all of the essential trace elements at the stated concentrations.

A preferred basal medium contains all twenty of the principal naturally occurring amino acids. Suitable ranges of concentrations are shown in the following table along with preferred and most preferred ranges.

| Elements | Minimum Concentrations (mg/L) | Preferred Range of Concentrations (mg/L) | Most Preferred Range of Concentrations (mg/L) |
|---|---|---|---|
| copper | $3.1 \times 10^{-10}$ | $3.1 \times 10^{-5}$–$3.1 \times 10^{-3}$ | $1.6 \times 10^{-4}$–$6.4 \times 10^{-4}$ |
| iron | $8.4 \times 10^{-8}$ | $8.4 \times 10^{-3}$–$8.4 \times 10^{-1}$ | $4.6 \times 10^{-2}$–$1.8 \times 10^{-1}$ |
| zinc | $9.9 \times 10^{-8}$ | $9.9 \times 10^{-3}$–$9.9 \times 10^{-1}$ | $4.9 \times 10^{-2}$–$1.9 \times 10^{-1}$ |
| manganese | $2.8 \times 10^{-11}$ | $2.8 \times 10^{-6}$–$2.8 \times 10^{-4}$ | $1.4 \times 10^{-5}$–$5.6 \times 10^{-5}$ |
| silicon | $7.0 \times 10^{-9}$ | $7.0 \times 10^{-4}$–$7.0 \times 10^{-2}$ | $3.5 \times 10^{-3}$–$1.4 \times 10^{-2}$ |
| molybdenum | $4.8 \times 10^{-11}$ | $4.8 \times 10^{-6}$–$4.8 \times 10^{-4}$ | $2.4 \times 10^{-5}$–$1.0 \times 10^{-4}$ |
| vanadium | $1.3 \times 10^{-10}$ | $1.3 \times 10^{-5}$–$1.3 \times 10^{-3}$ | $6.5 \times 10^{-5}$–$2.6 \times 10^{-4}$ |
| nickel | $1.4 \times 10^{-11}$ | $1.4 \times 10^{-6}$–$1.4 \times 10^{-4}$ | $7.5 \times 10^{-6}$–$3.0 \times 10^{-5}$ |
| tin | $3.1 \times 10^{-11}$ | $3.1 \times 10^{-6}$–$3.1 \times 10^{-4}$ | $1.5 \times 10^{-5}$–$6.0 \times 10^{-5}$ |
| aluminum | $1.3 \times 10^{-10}$ | $1.3 \times 10^{-5}$–$1.3 \times 10^{-3}$ | $6.5 \times 10^{-5}$–$2.6 \times 10^{-4}$ |
| silver | $1.1 \times 10^{-10}$ | $1.1 \times 10^{-5}$–$1.1 \times 10^{-3}$ | $5.0 \times 10^{-5}$–$2.2 \times 10^{-4}$ |
| barium | $1.4 \times 10^{-9}$ | $1.4 \times 10^{-4}$–$1.4 \times 10^{-2}$ | $7.0 \times 10^{-4}$–$2.8 \times 10^{-3}$ |
| bromine | $4.0 \times 10^{-11}$ | $4.0 \times 10^{-6}$–$4.0 \times 10^{-4}$ | $2.0 \times 10^{-5}$–$8.0 \times 10^{-5}$ |
| cadmium | $1.1 \times 10^{-9}$ | $1.1 \times 10^{-4}$–$1.1 \times 10^{-2}$ | $5.5 \times 10^{-4}$–$2.2 \times 10^{-3}$ |
| cobalt | $6.0 \times 10^{-10}$ | $6.0 \times 10^{-5}$–$6.0 \times 10^{-3}$ | $3.0 \times 10^{-4}$–$1.2 \times 10^{-3}$ |
| chromium | $5.3 \times 10^{-11}$ | $5.3 \times 10^{-6}$–$5.3 \times 10^{-4}$ | $2.5 \times 10^{-5}$–$1.1 \times 10^{-4}$ |
| fluorine | $2.3 \times 10^{-9}$ | $2.3 \times 10^{-4}$–$2.3 \times 10^{-2}$ | $1.2 \times 10^{-3}$–$4.6 \times 10^{-3}$ |
| germanium | $3.7 \times 10^{-10}$ | $3.7 \times 10^{-5}$–$3.7 \times 10^{-3}$ | $1.8 \times 10^{-4}$–$7.4 \times 10^{-4}$ |
| iodine | $4.1 \times 10^{-11}$ | $4.1 \times 10^{-6}$–$4.1 \times 10^{-4}$ | $2.0 \times 10^{-5}$–$8.2 \times 10^{-5}$ |
| rubidium | $8.5 \times 10^{-10}$ | $8.5 \times 10^{-5}$–$8.5 \times 10^{-3}$ | $4.2 \times 10^{-4}$–$1.7 \times 10^{-3}$ |
| zirconium | $9.0 \times 10^{-10}$ | $9.0 \times 10^{-5}$–$9.0 \times 10^{-3}$ | $4.5 \times 10^{-4}$–$1.8 \times 10^{-3}$ |
| selenium | $2.6 \times 10^{-9}$ | $2.6 \times 10^{-4}$–$2.6 \times 10^{-2}$ | $1.3 \times 10^{-3}$–$5.1 \times 10^{-3}$ |

The trace element mixture of the invention may be prepared in solid or liquid form for ease of addition to a basal medium. For long-term storage, a solid preparation comprising an intimate mixture of trace elements, optionally with a water-soluble filler for ease of measurement, is preferred because of stability. Suitable solid fillers include any of the inorganic salts or other solids hereafter discussed as being useful in basal culture media. If desired, the mixture may be prepared in one or more groupings of elements to be added individually during the preparation of a protein-free medium. In order to provide the intimate mixing necessitated by the minute quantities of these trace elements, it is preferred to prepare an aqueous solution of the trace elements, optionally with a filler as described above, and to reduce the aqueous solution to dryness, thereby intimately mixing all components.

For ease of addition to basal media, liquid preparations are preferred. Stock solutions of the individual trace elements or of mixtures thereof can be prepared which can then be added to a basal medium by pipet.

The basal medium used for the present invention may be either a commercially available medium or may be prepared from individual starting materials. A basal medium is prepared by combining at least one component from the group consisting of amino acids, inorganic salts, vitamins, buffering agents, antibiotics, and other nutrients of known high value in facilitating the growth of hybridoma cells and other cells that produce biologically or clinically useful products into a basal medium into which the trace elements are added. Some

| Amino Acids | Suitable[a] Range | Preferred Range | Most Preferred Range |
|---|---|---|---|
| L-alanine | 0.2+ | 1.7–170 | 8.5–34 |
| L-arginine | 1.5+ | 14.7–1470 | 74–295 |
| L-asparigine[1] | 0.2+ | 2.0–200 | 10–40 |
| L-aspartic acid[1] | 0.2+ | 2.2–220 | 11–43 |
| L-cystine[2] | 0.1+ | 1.1–110 | 5.5–22 |
| L-cysteine[2] | 0.5+ | 4.9–490 | 24–98 |
| L-glutamic acid[3] | 0.4+ | 4.5–450 | 22–90 |
| L-glutamine[3] | 3.7+ | 36.5–3650 | 192–730 |
| glycine | 0.1+ | 1.1–110 | 5.5–23 |
| L-histidine | 0.3+ | 3.2–320 | 16–63 |
| L-isoleucine | 0.5+ | 5.4–540 | 27–109 |
| L-leucine | 0.6+ | 5.9–590 | 29–118 |
| L-lysine | 0.9+ | 9.1–910 | 46–183 |
| L-methionine | 0.2+ | 1.7–170 | 8.5–34 |
| L-phenylalanine | 0.4+ | 3.5–350 | 18–71 |
| L-proline | 0.4+ | 3.7–370 | 19–75 |
| L-serine | 0.3+ | 2.6–260 | 13–53 |
| L-threonine | 0.5+ | 5.3–530 | 27–106 |
| L-tryptophan | 0.09+ | 0.9–90 | 4.5–18 |
| L-tyrosine | 0.5+ | 5.2–520 | 26–104 |
| L-valine | 0.5+ | 5.3–530 | 26–106 |

Notes:
[a] In this and all following tables, a number followed by a + under a concentration heading indicates that the upper limit is determined by solubility in the total basal medium.
[1] Either asparagine or aspartic acid may be eliminated if compensated by a corresponding increase in the retained component.
[2] Either cystine or cysteine may be eliminated if compensated by a corresponding increase in the retained component.
[3] Either glutamine or glutamic acid may be eliminated if compensated by a corresponding increase in the retained component.

Preferred embodiments of the basal medium employ all twenty of amino acids as shown above. However, as is well recognized by those skilled in the art, one or more of the amino acids may not be required by certain cell lines. Accordingly, it is possible to produce a basal medium suitable for the growth of certain cells by eliminating non-essential amino acids. A basal medium containing all twenty amino acids is preferred merely because it allows the use of the same basal medium with different types of cell lines without requiring supplementation of the basal medium with different essential amino acids when it is used with various cell lines.

Another group of common ingredients which are present in hybridoma cell media are inorganic ions which are not regarded as trace elements because of their higher concentrations, such as calcium, potassium, magnesium, sodium, chloride, phosphate, and carbonate ions. These ions are added as salts, generally as water-soluble nitrate or sulfate salts of the positive ions listed. The negative ions, such as chloride, phosphate, and carbonate, are generally added as sodium or potassium salts. However, a great deal of discretion is available in selecting the inorganic salts. The concentrations of inorganic salts can vary widely, limited principally by the necessity of maintaining a suitable osmolarity in the culture medium. A suitable range of osmolarities (ionic strengths), if not already known for the cell type being culture, can be determined by simple experimentation. The following table gives suitable, preferred and most preferred concentrations for preferred embodiments of the present invention. As is well recognized by those skilled in the art of culture medium preparation, cells may remain viable when these ions are present in ranges outside those suitable for use with preferred embodiments of the invention, and such concentrations are also contemplated as being equivalent to concentrations of the present invention.

| Inorganic salts[1] | Concentration Ranges (mg/L) | | |
|---|---|---|---|
| | Suitable Range | Preferred Range | Most Preferred Range |
| $Ca^{2+}$ | 0.36–3600 | 9.0–144 | 18–72 |
| $K^+$ | 1.76–17,300 | 43–690 | 86–345 |
| $Mg^{2+}$ | 0.17–1720 | 4.3–69 | 8.6–35 |
| $Na^+$ | 30–3.0 × 10⁵ | 750–12,000 | 1500–6000 |
| $Cl^-$ | 39–3.9 × 10⁵ | 975–15,600 | 1950–7800 |
| $PO_4^{3-}$[2] | 0.96–10,000 | 24–400 | 48–192 |
| $HCO_3^-$[3] | 15–1.5 × 10⁵ | 380–6100 | 760–3050 |

[1] In addition to the ranges given for individual ions, the total inorganic salt concentration (including trace elements) does not give an ionic strength outside the stated limits for the given ranges.
[2] Includes $HPO_4^{2-}$ and $H_2PO_4^-$.
[3] Includes $CO_3^{2-}$; added as carbonate or bicarbonate salt.

A cell growth medium may contain other ingredients necessary or desirable for cell growth. These include vitamins and other supplements such as essential fatty acids, growth-promoting hormones, and antibiotics. Many of these are cofactors for the enzymes normally present in the cells being cultivated and may be added as necessary. However, preferred basal media of this invention contain a broad range of vitamins and other supplements in order that a general basal medium is provided which need not be further supplemented when changing from one cell line to another. The following table lists suitable, preferred and most preferred concentration ranges of vitamins and other supplements present in the preferred basal media of the invention. This listing is not intended, however, to be fully inclusive of the broad scope of the present invention but only of its preferred embodiments.

| | Concentration Ranges (mg/L unless otherwise noted) | | |
|---|---|---|---|
| | Suitable Range | Preferred Range | Most Preferred Range |
| Vitamins | | | |
| Biotin | $1.0 \times 10^{-4}$–1.0 | $2.5 \times 10^{-3}$–0.040 | $5.0 \times 10^{-3}$–0.020 |
| pantothenate | 0.022–225 | 0.56–9.0 | 1.1–4.5 |
| choline | 0.090–900 | 2.3–36 | 4.6–18 |
| folic acid | 0.027–275 | 0.66–10.6 | 1.3–5.3 |
| inositol | 0.12–1250 | 3.1–50 | 6.2–25 |
| nicotinamide | 0.020–200 | 0.50–8.0 | 1.0–4.0 |
| pyridoxal | 0.020–200 | 0.50–8.0 | 1.0–4.0 |
| pyridoxine | $3.1 \times 10^{-4}$–3.1 | $7.8 \times 10^{-3}$–0.12 | 0.015–0.060 |
| riboflavin | $2.2 \times 10^{-3}$–22 | 0.055–0.88 | 0.11–0.44 |
| thiamine | 0.022–220 | 0.55–8.8 | 1.1–4.4 |
| vitamin $B_{12}$ | $6.9 \times 10^{-3}$–69 | 0.17–2.7 | 0.34–1.4 |
| Other Supplements | | | |
| pyruvate | 1.1–11,000 | 28–450 | 56–225 |
| glucose | 14–1.4 × 10⁵ | 350–5600 | 700–6300 |
| phenol red | 0.1–1000 | 2.6–43 | 5.2–22 |
| putrescine | $8.1 \times 10^{-4}$–8.1 | 0.020–0.32 | 0.040–0.16 |
| hypoxanthine | 0.020–200 | 0.50–8.0 | 1.0–4.0 |
| linoleic acid | $4.1 \times 10^{-4}$–4.1 | 0.010–0.16 | 0.020–0.080 |
| lipoic acid | $1.0 \times 10^{-3}$–12 | 0.025–0.4 | 0.050–0.2 |
| thymidine | $3.6 \times 10^{-3}$–37 | 0.091–1.5 | 0.18–0.75 |
| penicillin | 1–10,000 U/ml | 25–400 U/ml | 50–200 U/ml |
| streptomycin | 1–10,000 μg/ml | 25–400 μg/ml | 50–200 μg/ml |
| α-thioglycerol | 0.063 μL/L–625 μL/L | 1.6 μL/L–25 μL/L | 3.2 μL/L–13 μL/L |
| progesterone | $1.0 \times 10^{-4}$–1.0 | $2.5 \times 10^{-3}$–0.040 | $5.0 \times 10^{-3}$–0.020 |

It is also preferred to use a buffering agent, in addition to the $HCO_3^-/CO_2$ system, in media of the invention, although this is not essential. Various buffering agents may be used although HEPES buffer is preferred. HEPES is N'-2-hydroxyethylpiperazine-N'-ethanesulfonic acid. A pH range of 7.0–7.7 is preferred with a range of 7.2–7.5 being more preferred and a range of 7.3–7.4 being most preferred.

Growth media may be maintained at any temperature between 4° C. and 40° C. The temperature is preferably selected according to the specific cell type being cultured. Typical cultivation is at 37°±1° C.

Although the preferred embodiments of this invention are related to hybridoma cell lines, such as those which produce monoclonal antibodies, and to other cell types which produce substances of clinical or biological importance, the media of this invention are, in their broadest aspects, media of defined composition which can be used for any purpose for which such media are typically used, for example, in maintaining the short- or long-term growth of any cell or cell line. Preferred are animal cells, particularly mammalian cells, with so-called "immortal" cell lines being most preferred because of the characteristics described herein which make these media particularly well suited for such cell lines.

Cells are grown in the media of the invention using conventional techniques and methods. When a cell not previously grown in a media of the invention is obtained, it will usually be from a medium supplemented with serum or serum proteins. Although some cells will undoubtedly survive when transferred directly to a protein-free medium of the invention, generally more successful results will be obtained if the serum concentration is lowered gradually. This may be done in any method which eventually results in the cells being cultivated in a protein-free medium of the invention. However, the following technique is generally convenient.

Cells obtained from a medium containing serum are grown in the basal medium which will eventually be supplemented with the trace element mixture of the invention but which is initially supplemented with 10% fetal calf serum rather than the trace element mixture. When the cells grow to form a monolayer with excess cells in suspension, all medium and unattached cells are removed by pipette. Then an equal volume of fresh medium containing ½ the former serum amount but otherwise being the complete protein-free medium, including the trace element mixture, is added back to the flask. This procedure is repeated until the serum concentration is reduced to less than 0.1%, after which feeding with basal medium supplemented only with trace elements may be carried out.

New culture flasks may be prepared by taking a portion of the old medium containing unattached cells and adding this portion to a new culture flask along with an equal volume of fresh medium of the same type and serum concentration (including the protein-free culture media of the invention).

It will be recognized by those skilled in the art of hybridoma cell line cultivation that not all cell lines will survive and grow in any one specific protein-free basal medium supplemented with the trace element mixture as disclosed in the present invention. However, all but one of the hybrid or myeloma cell lines so far tested have survived and grown in a basal medium supplemented with trace elements as described for the present invention. Both hybridomas and myelomas have been tested as well as cell lines that product cytokines. A summary of the results is presented in Table IV in the Examples section of this application.

In a preferred embodiment of the present invention, cells are grown in attached monolayers in a cell medium of the invention. In fact, the medium facilitates attachment of cells to substratum. This is true even for cell lines which grow unattached in other media. The use of attached monolayers with media of the invention maintains high cell densities. Recovery of cells can be accomplished by shaking or forceful pipetting. Trypsinization is not necessary, thereby avoiding the special care that is required when trypsinization is carried out in a protein-free medium. Media of the invention, therefore, are particularly useful in facilitating the application of automatic fermentation devices and microcarrier beads for the production in protein-free media of the multigram quantities of monoclonal antibodies needed for clinical purposes. The ease of inducing attachment in protein-free media of this invention is a distinct advantage over existing procedures which employ elaborate and difficult measures for anchoring hybridoma cells.

The invention now being generally described, the same will be better understood by reference to certain specific examples which are included herein for purposes of illustration only and are not intended to be limiting of the invention or any embodiment thereof, unless specified.

EXAMPLE I:

Preparation of Protein-Free Medium

Water used for preparation of media was glass-distilled after it had been passed through a particle filter followed by a charcoal cartridge and a mixed bed ion exchange resin cartridge (Continental Water Conditioning Corp.). Storage was in a glass bottle. The basal medium (BM) was prepared on a 2 liter scale as follows: the contents of a 1 liter size packet of F12 (Ham, *Proc. Natl. Acad. Sci. U.S.A.*, 75: 288 (1965)) (Gibco) were added to 950 ml of $H_2O$ in a glass 1 liter graduate cylinder with stirring (teflon spin bar). The pH was adjusted to 7.3 using 5 or 10 $\mu l$ aliquots of 10N NaOH and the contents of a 1 liter size packet of IMDM (Gibco) were added, with stirring. Then the following additions were made: 4.20 g of $NaHCO_3$ (Fisher), 20 ml of 100×Pen-Strep mixture (Gibco), 12.5 $\mu l$ of α-thioglycerol (Sigma), 10 $\mu l$ of a 2 mg/ml solution of progesterone (Sigma) in 100% ethanol (stable at $-20°$ C. for at least a year). The stock was then brought to 2 liters with water and sterilized by vacuum filtration (0.45 $\mu m$, Nalgene 2450045 filter). BM could be stored at 4° C. in darkness for at least a month before the addition of trace elements or other supplements and its subsequent use over an additional month. The composition of BM is shown in the following table.

TABLE

| Final Composition of Modified Iscove/F12 Medium | | | |
|---|---|---|---|
| Amino Acids | Mg/Liter | Inorganic Salt | Mg/Liter |
| L-Alanine | 16.95 | $CaCl_2$ | 99.11 |
| L-Arganine.HCl | 147.5 | $CuSO_4.5H_2O$ | 0.00125 |
| L-Asparagine.$H_2O$ | 21.71 | $FeSO_4.7H_2O$ | 0.4170 |
| L-Aspartic acid | 21.65 | | |
| L-Cystine.2HCl | 45.62 | KCl | 276.8 |
| L-Cysteine.HCl.$H_2O$ | 17.56 | | |
| L-Glutamic acid | 44.85 | $MgCl_2$ | 28.61 |
| L-Glutamine | 365.0 | $MgSO_4$ | 48.83 |
| Glycine | 18.75 | NaCl | 6052.0 |
| L-Histidine HCl.$H_2O$ | 31.48 | $Na_2HPO_4$ | 71.02 |
| L-Isoleucine | 54.47 | $NaH_2PO_4.H_2O$ | 62.5 |
| L-Leucine | 59.05 | $ZnSO_4.7H_2O$ | 0.4315 |
| L-Lysine HCl | 91.25 | $NaHCO_3$ | 2100.0 |
| L-Methionine | 17.24 | $Na_2SeO_3.5H_2O$ | 0.00865 |
| L-Phenylalanine | 35.48 | | |
| L-Proline | 37.25 | | |
| L-Serine | 26.25 | | |
| L-Threonine | 53.45 | | |
| L-Tryptophan | 9.02 | | |

TABLE-continued
Final Composition of Modified Iscove/F12 Medium

| | Mg/Liter | | |
|---|---|---|---|
| L-Tyrosine.Na$_2$ | 55.79 | | |
| L-Valine | 52.85 | | |

| Vitamins | Mg/Liter | Other Supplements | Mg/Liter |
|---|---|---|---|
| Biotin | 0.010 | Sodium pyruvate | 110.0 |
| D-Ca—panthothenate | 2.24 | Glucose | 3151.0 |
| Choline chloride | 8.98 | Phenol red | 8.1 |
| Folic acid | 2.65 | Putrescine.2HCl | 0.081 |
| I—Inositol | 12.6 | Hypoxanthine | 2.39 |
| Nicotinamide | 2.02 | Linoleic acid | 0.042 |
| Pyridoxal.HCl | 2.0 | Lipoic acid | 0.105 |
| Pyridoxine.HCl | 0.031 | Thymidine | 0.365 |
| Riboflavin | 0.219 | Hepes | 2979 |
| Thiamine.HCl | 2.17 | | (12.5 mM) |
| Vitamin B$_{12}$ | 0.687 | | |

For cultivation under protein-free conditions, BM was supplemented with trace elements, which could be prepared as stock solutions and stored at 4° C. for more than a year. For convenience, the trace element mixtures were prepared in two batches which were added separately to the basal medium. These trace element mixtures are hereafte referred to as TEI and TEII, respectively, and their compositions are shown in Tables I and II.

TABLE I
COMPOSITION OF TRACE ELEMENT MIXTURE TEI

| Substance | Source[a] | Stock Solutions (mg/100 ml) | Volume for 1000 × TEI[b] |
|---|---|---|---|
| MnSO$_4$.H$_2$O | Me | 17 | 0.1 ml |
| Na$_2$SiO$_3$.9H$_2$O | JTB | 28 | 50.0 ml |
| (NH$_4$)$_6$Mo$_7$O$_{24}$.4H$_2$O | Fi | 124 | 0.1 ml |
| NaVO$_3$ | Fi | 12 | 0.5 ml |
| NiSO$_4$.6H$_2$O | Fi | 26 | 0.05 ml |
| SnCl$_2$.2H$_2$O | Ma | 23 | 0.05 ml |

[a]Me = Merck; JTB - J. T. Baker, Fi = Fisher, Ma = Mallinkrodt
[b]The indicated volumes were added to a polystyrene tissue culture flask and the volume brought up to 100 ml with cell culture H$_2$O. Then 5μ of concentrated HCl was added and the mixture passed through a 0.45 μm Nalgene filter funnel and stored at 4° C.

TABLE II
COMPOSITION OF TRACE ELEMENT MIXTURE TEII

| Substance | Source[a] | Stock solutions (10$^5$ X) (mg/100 ml)[b] |
|---|---|---|
| AlCl$_3$.6H$_2$O | JTB | 12.0 |
| AgNO$_3$ | Fi | 1.7 |
| Ba(C$_2$H$_3$O$_2$)$_2$ | JTB | 25.5 |
| KBr | H | 1.2 |
| CdCl$_2$.2.5H$_2$O | JTB | 22.8 |
| CoCl$_2$.6H$_2$O | JTB | 23.8 |
| Cr(SO$_4$)$_3$.nH$_2$O | JTB | 6.6 |
| NaF | JTB | 42.0 |
| GeO$_2$ | Fl | 5.3 |
| Ki | Ma | 1.7 |
| RbCl | Fl | 12.1 |
| ZrOCl$_2$.8H$_2$O | BDH | 32.2 |

[a]JTB = J. T. Baker, Fi = Fisher, H = Harshaw, Fl = Fluka, Ma = Mallinkrodt, BDH = British Drug Houses.
[b]1 ml of each stock solution was added to a culture flask and the volume was brought up to 100 ml using cell culture H$_2$O. This solution was sterile filtered and stored at 4° C. and used as a 1000X working stock solution; i.e., 1000X TEII.

In some later-described experiments, the basal medium was supplemented with transferrin (Tf), insulin (ins), and liposomes (L). A 1000×stock solution (5 mg/ml) of human transferrin (Sigma) was prepared by dissolving 50 mg of transferrin in 10 ml of basal medium. It was filter-sterilized (Gelman, Acrodisc, 0.45 μm) and stored at 4° C. The insulin stock solution (500×) was prepared by adding 25 mg of bovine insulin (Schwarz-Mann, 25.9 U/mg) to 10 ml of Dulbecco's PBS (Dulbecco and Vogt, *J. Exp. Med.*, 99: 167 (1954)) (Gibco) followed by the addition of small aliquots of freshly made, saturated Na$_2$CO$_3$ until the insulin was dissolved. The final pH was about 9.5. After sterilization by filtration, the solution could be stored at 4° C. for at least a year. Liposomes were prepared according to the procedure of Iscove and coworkers (Iscove and Melchers, supra; Iscove et al., *Exp. Cell Res.*, 126: 121 (1980)), using crystalline bovine albumin (Sigma) and synthetic lipids: L-α-dipalmitoyl phosphatidylcholine, cholesterol and either linoleic acid or oleic acid, all from Sigma. Liposome preparations were used at a dilution of 1/250. Those made with oleic acid could be used interchangeably with those made with linoleic acid, without obvious differences.

EXAMPLE II
Growth of Cells in Protein-Free Culture Media
Materials and Methods Cells were received from their sources (Table III) in media that were usually supplemented with 10% serum. After initial growth in 1 ml size Linbro wells (Flow Labs. No. 76-033-05), they were transferred to culture flasks (Lux No. 5375, 75 cm$^2$) and grown in BM+½ TEI+TEII+10% FCS (20 ml/flask). Attached growth was readily obtained with rat/mouse and mouse/mouse hybridomas and also mouse myeloma cells. The firmness of attachment was adequate for feeding manipulations but was such as to allow recovery of the adherent cells in a viable form by forceful pipetting, without trypsinization. When the monolayer was saturated with cells, excess cells grew in suspension. For feeding, a flask was placed in a vertical position and all medium, together with unattached cells, was removed by pipette. Then 20 ml of fresh medium (see below for choice of medium) was promptly added to the flask, directing the stream of liquid away from the cell monolayer to avoid dislodging the cells. In general, a Monday-Wednesday-Friday feeding schedule was followed. New flasks could be started by adding 10 ml of fresh medium followed by 10 ml of old medium+unattached cells, obtained on a feeding day from a flask containing a healthy and dense monolayer of cells. The above-described procedures could be done with cells grown in any medium formulation, including the protein-free medium. Moreover, no decline in the capacity to start new flasks was noticed with cells that had been grown in protein-free medium for an extended period. To obtain cells for cryopreservation, attached cells were disloged by forceful pipetting (no trypsinization). Gel electrophoresis (SDS-PAGE) was carried out according to the method of Laemmli, *Nature (London)*, 256: 495 (1970), under non-reducing conditions using 7.5% acrylamide gels that were 3 mm thick. Sample volumes were 50 μl in all cases.

TABLE III

| | CELL LINES TESTED FOR GROWTH IN SERUM FREE AND PROTEIN FREE MEDIA | | | |
|---|---|---|---|---|
| Cell Line | Type of Cells | Ig Class | Reference[b] | Source[c] |
| 53-7.313 | Rat/mouse hybrid | Rat IgG$_{2a}$ | Ledbetter and | S.I. |

TABLE III-continued
CELL LINES TESTED FOR GROWTH IN SERUM FREE AND PROTEIN FREE MEDIA

| Cell Line | Type of Cells | Ig Class | Reference[b] | Source[c] |
|---|---|---|---|---|
| 53-6.72 | Rat/mouse hybrid | Rat IgG$_{2a}$ | Herzenberg (1979) Ledbetter and Herzenberg (1979) | S.I. |
| 30-H12 | Rat/mouse hybrid | Rat IgG$_{2b}$ | Ledbetter and Herzenberg (1979) | S.I. |
| MI/70.15.1 | Rat/mouse hybrid | Rag IgG$_{2b}$ | Springer (1980) | S.I. |
| MI/75.16.4 | Rat/mouse hybrid | Rat IgG$_{2c}$ | Springer (1980) | S.I. |
| MI/69.16.11 | Rat mouse hybrid | Rat IgG$_{2b}$ | Springer (1980) | S.I. |
| 331.12 | Rat mouse hybrid | Rat IgG$_{2b}$ | Kincade et al (1972) | S.I. |
| 2b-187.1 | Rat/mouse hybrid | Rat IgG$_{2c}$ | Yelton et al (1981) | M. S. |
| HO13-4-9 | Mouse/mouse | Mouse IgM | Marshak-Rothstein et al (1979) | S.I. |
| Hyl[a] | Mouse/mouse | Mouse IgM | | |
| 456,31 | Mouse myeloma | IgG$_{2b}$ | Laskov and Scharff (1970) | S. Z. P. |
| P3X63-Ag8.653 | Mouse myeloma | — | Kearney et al (1979) | E. K. |
| Ehrlich ascites | Mouse tumor | α, β-interferon | Slattery et al (1980) | S. Mo. |
| Friend leukemia | Mouse | — | Friend et al (1971) | C. F. |
| BFS | Mouse T-cell | γ-interferon | Benjamin et al (1982) | J. O. |
| P388D | Mouse macrophage | IL-1 | Mizel et al (1981) | S. Mi. |
| WEHI-3 | Mouse tumor | IL-3 | Ihle et al (1981) | J. I. |

[a]Hyl is a line that was isolated in the inventors' laboratory. It produces monoclonal antibody that is specific for 5-methylcytidine (unpublished).
[b]References: Ledbetter and Herzenberg, Immunol. Rev., 47, 362 (1979); Springer, in Monoclonal Antibodies, eds. Kennett et al; Plenum Press, N.Y., p. 185, 1980; Kincade et al, J. Immunol Methods, 42, 1 (1981); Yelton et al, Hybriboma, 1, 5 (1981); Marchak-Rothstein et al, J. Immunol., 122, 2491 (1979); Laskov and Scharff, J. Exp. Med., 131, 515 (1970); Kearney et al, J. Immunol., 123, 1548 (1979); Slattery et al, J. Gen. Virol., 49, 91–96 (1980); Friend et al, Proc. Natl. Acad. Sci. USA, 68, 378–382 (1971); Benjamin et al, ibid, 79, 5379–5383 (1982); Mizel and Mizel, J. Immunol., 126, 384 (1981); Ihle et al, ibid, 126, 2184 (1981).
[c]S.I. = Salk Institute, M. S. = Dr. Matthew Scharff;, S. Z. P. = Dr. Susan Zolla-Pasner, E. K. = Dr. Elvin Kabat, who obtained this line from Dr. G. Kohler, S. Mo. = Dr. S. Moshowitz, C. F. = Dr. C. Friend, J. O. = Dr. J. Oppenheim, S. Mi. = Dr. S. B. Mizel, J. I. = Dr. J. N. Ihle.

The IgG$_{2b}$ protein of the myeloma line 456 was isolated from ascites fluid with a protein A-Sepharose (Pharmacia) column according to the procedure of Ey et al., *Immunochemistry*, 15: 429 (1981), and used to prepare concentration standards for IgG. Protein concentration was calculated from the optical density at 280 nm, assuming an O.D. (280) of 1.4 for a 1.0 mg/ml solution.

A human IgM protein (Waldenstrom macrogolbulin) was isolated from plasma using euglobulin precipitation followed by chromatography on a Sephacryl S-300 (Pharmacia) column. Protein concentration was determined as above. Solutions of this protein, diluted in culture medium were used as concentration standards of IgM.

Results

A flask (75 cm$^2$) that was started with cells in BM +½ TEI+TEII+10% FCS was fed with this medium until a dense monolayer of healthy cells was obtained. The flask was then fed with BM+½ TEI+TEII containing 1% FCS. Cultivation in this medium was continued for 2 weeks or longer, depending on the condition of the monolayer, before further reduction of serum concentration.

In several early studies, cell lines that had been grown in BM+1% FCS were transferred directly to BM+½ TEI+Ins+Tf+L, a process that yielded an approximate 20-fold dilution of the serum. This was done by removing all medium except for that adhering to the walls of the flask, and replacing it with fresh medium. With several hybridoma lines (e.g., 53-7.313, 53-6.72, HO13-4-9, 2b-187.1 and Hy 1), this sudden reduction in the serum concentration caused only a slight temporary deterioration of the monolayers. Similar results were obtained when lines that were growing well in BM+½ TEI+Ins+Tf+L were switched to other serum free formulations such as BM+½ TEI+TEII+Ins+Tf or BM+½ TEI+TEII+Ins.

More recently cells growing in BM+1% FCS have been switched to BM+½ TEI+TEII+Ins or BM+½ TEI+TEII without an intermediate period of growth in media supplemented with transferrin, insulin and liposomes. In some cases, it has been possible to change rapidly to the protein-free medium. For example, cells of line 2b-187.1 tolerated direct transfer to BM+½ TEI+TEII (20-fold dilution factor at first and subsequent feedings). However, in the case of another line, 456.31, direct transfer from BM+1% FCS to BM+½ TEI+TEII+Ins led to a massive destruction of the monolayer cells. A few cells evidently survived since the flask eventually recovered and produced high levels of Ig. Nevertheless, sudden changes in medium composition with all lines is preferably avoided in order to avoid selective pressures that might favor Ig non-producers. Because of variations in individual lines and even in different flasks of the same line, changes in protocol have been required. The serum concentration in a flask is preferably reduced by feeding with mixtures of BM+½ TEI+TEII+1% FCS and BM+½ TEI+-TEII. Serum concentration is reduced by no more than a factor of 2 or 3 in a single step. If monolayer deterioration is observed at some point, further reduction in the serum concentration is avoided until the flask shows a high density of cells in the monolayer and exhibits vigorous growth of cells as indicated by medium acidification. Then further gradual reduction of serum is continued.

All of the lines tested were found, on the basis of microscopic observations, to grow well in BM+FCS. All but one, Ml/75.16.4, grew in serum-free media. This line was tested with 3 different serum-free formulations (BM+½ TEI+Ins+Tf+L, BM+½ TEI+-TEII+Ins+Tf, BM+½ TEI+TEII) and quickly died in all of them. All other cell lines tested could be successfully grown in one or more of the serum-free or protein-free formulations (Table IV).

centration standards: 5, 10, 25, 50, 100 μg/ml, respectively. Lane 7: culture supernatant of line 53-6.72 (BM+½ TEI+TEII), after 18 days. Lane 8: 53-6.72 (BM+½ TEI+Ins+Tf+L). Lane 9: 53-6.72 (BM+1% FCS). Lane 10: culture supernatant of line 53-7.313 (BM+½ TEI+TEII), after 10 days. Lane 11: 53-7.313

TABLE IV

| Cell Line | Ig Produced in Medium (μg/ml) | | | | | |
|---|---|---|---|---|---|---|
| | BM + 1% FCS | BM + 0.1 FCS | BM + ½ TEI + Ins + Tf + L | BM + ½ TEI + TEII + Ins + Tf | BM + ½ TEI + TEII + Ins | BM + ½ TEI + TEII |
| 53-7.313 | 50–100 | NT[b] | 75–150 (56) | NT | NT | 50–100 (18) |
| 53-6.72 | 75–150 | NT | 75–150 (42) | NT | NT | 20–50 (33) |
| 30-H12 | +[a] | NT | + (63) | NT | NT | NT |
| M1/70.15.1 | + | + (28)[c] | 50–100 (45) | 50–100 (45) | 50–100 (82) | 50–100 (185) |
| M1/75.16.4 | + | NT | −[d] | − | NT | − |
| M1/69.16.11 | 50–100 | 20–50 (67) | NT | 50–100 (90) | 20–50 (69) | + (30) |
| 331.12[e] | + | + (18) | NT | + (50) | + (82) | + (14) |
| 2b-187.1 | 20–50 | NT | 50–100 (30) | NT | NT | 20–50 (40) |
| HO13-4-9 | 100–150 | NT | + | NT | NT | 100–150 (103) |
| Hy 1[f] | 75–150 | NT | + (56) | NT | NT | 50–100 (120) |
| 456,31 | 100–200 | 75–150 (49) | 100–200 (45) | 100–200 (45) | 150–200 (78) | 150–200 (223) |
| P3X63-Ag8.653 | + | NT | NT | NT | NT | + (34) |

[a] + indicates successful growth; Ig production not evaluated.
[b] NT indicates cell line not tested with indicated medium formulation.
[c] Numbers in parentheses refer to numbers of days of growth in indicated media.
[d] − indicates failure to grow.
[e] This line ceased to produce Ig soon after being received in the inventor's laboratory. It was therefre only tested for growth.
[f] This line has so far been grown in protein-free medium only on a small scale (1 ml) in Linbro wells. Under these conditions, it has grown in stationary suspension culture. Previously, before it was frozen, it was grown in BM + ½ TEI + Ins + Tf + L as an attached monolayer in 75 cm² flask.

In addition to microscopic observation, successful growth of cells in the various serum-free formulations was determined by semiquantitative measurement of immunoglobulin production by SDS-PAGE analyis. FIGS. 1a, b, c and 2 show the SDS-polyacrylamide gels thar were used to evaluate Ig production.

Figure 1B:
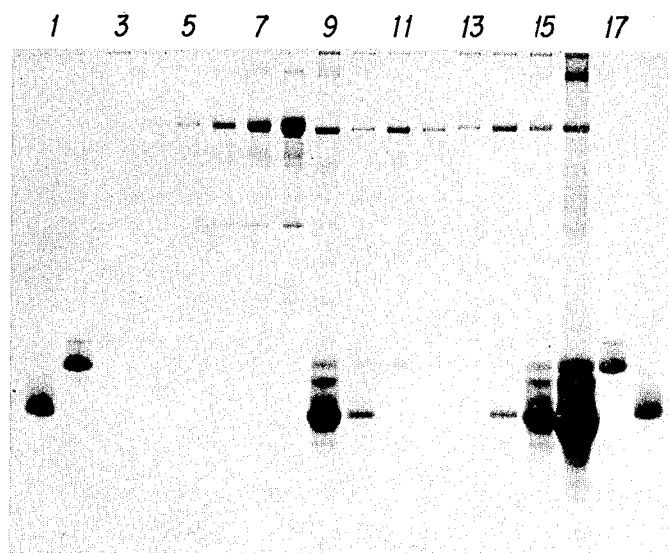
Figure 1C:
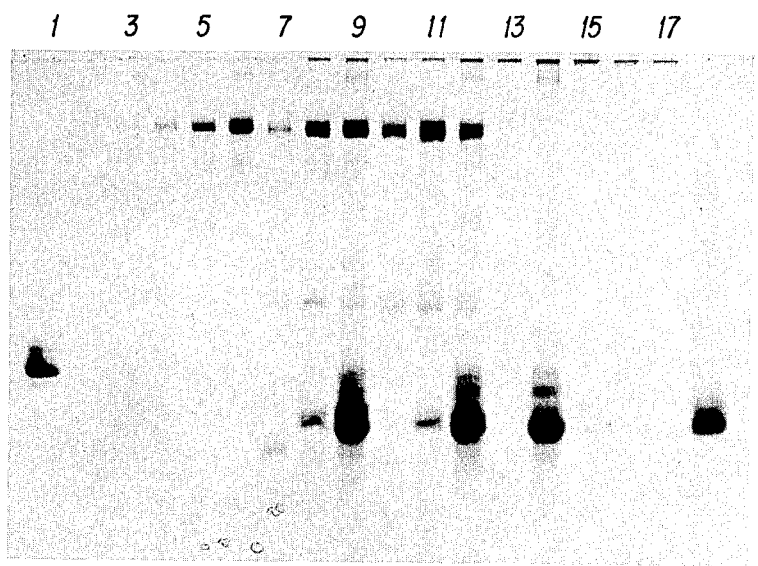

FIG. 1a shown a SDS-PAGE analysis of Ig production by lines 456,31 and HO13-4-9 in serum-supplemented, serum-free and protein-free media. Lane 1: BSA and Tf (MW=67,000 and 90,000 respectively). Lanes 2–5, purified mouse IgG$_{2b}$ concentration standards, 200, 100, 50, 20 μg/ml, respectively. Lane 6: culture supernatant of line 456,31 (BM+1% FCS). Lane 7: 456,31 (BM+0.1% FCS), after 42 days. Lane 8: 456,31 (BM+½ TEI+Ins+TF+L), after 25 days. Lane 9: 456,31 (BM+½ TEI+TEII+Ins+Tf), after 12 days. Lane 10: 456,31 (BM+½ TEI+TEII+Ins), after 55 days. Lane 11: 456,31 (BM+½ TEI+TEII), after 101 days. Lanes 12–14: purified IgM concentration standards: 100, 50 and 25 μg/ml, respectively. Lane 15: culture supernatant of line HO13-4-9 (BM+5% FCS). Lane 16: HO13-4-9 (BM+1% FCS). Lane 17, HO13-4-9 (BM+½ TEI+TEII), after 10 days. FIG. 1b shows an SDS-PAGE analysis of Ig production by lines M1/69.16.11 and 2b-187.1 in serum supplemented, serum-free and protein-free media. Lane 1: BSA (MW= 67,000). Lane 2: Tf (MW=90,000). Lanes 3–8: purified mouse IgG$_{2b}$ concentration standards: 5, 10, 20, 50, 100, 200 μg/ml, respectively. Lane 9: culture supernatant of line M1/69.16.11 (BM+1% FCS). Lane 10: M1/69.16.11 (BM+½ TEI+Ins+Tf+0.1% FCS), after 27 days. Lane 11: M1/69.16.11 (BM+½ TEI+-TEII+Ins+Tf). Lane 12: M1/69.16.11 (BM+½ TEI+-TEII+Ins), after 5 days. Lane 13: culture supernatant of line 2b-187.1 (BM+½ TEI+TEII), after 10 days. Lane 14: 2b-187.1 (BM+½ TEI Ins+Tf+L). Lane 15: 2b-187.1 (BM+1% FCS+Tf). Lane 16: 2b-187.1 (BM+10% FCS). Lane 17: Tf. Lane 18: BSA. FIG. 1c shows an SDS-PAGE analysis of Ig production by lines Hyl, 53-6.72 and 53-7.313 in serum-supplemented, serum-free and protein-free media. Lane 1: Tf (MW=90,000). Lanes 2–6: purified mouse IgG$_{2b}$ con- (BM+½ TEI+Ins+Tf+L). Lane 12: 53-7.313 (BM+Tf+1% FCS). Lane 13: culture supernatant of Hyl (BM+½ TEI+TEII), after 45 days. Lane 14: Hyl (BM+Tf+1% FCS). Lanes 15–17: IgM concentration standards: 100, 50, 25 μg/ml, respectively. Lane 18: BSA (MW=67,000).

Ig concentrations in untreated culture supernatants harvested on feeding days from flasks containing saturated monolayers of cells were estimated by visual comparison of hybridoma Ig bands with bands obtained by using purified Ig at known concentrations. These data are given in Table IV. In the case of IgM, comparisons were considered meaningful only with supernatants from cultures fed with serum-free or protein-free media, as serum-supplemented media contained substantial amounts of material that banded at the same position as the cell-produced IgM. Inspection of lanes on the sam gel obtained with IgG-containing serum-free supernatants revealed that the amounts of material which banded at the top of the gel were sufficiently small to allow at least a rough estimate of IgM concentrations in media not containing serum. As indicated, Ig production in serum-free and protein-free media for all lines tested was comparable to that achieved with serum-supplemented media. These gels also reveal the substantial improvement in the relative homogeneity of the antibody-containing supernatants that are obtained with serum-free and especially protein-free media. (For example, compare lanes 15 and 17 of FIG. 1a) It should be noted that 10 out of 11 lines tested with the protein-free formulation could be successfully grown in this medium, suggesting it may have wide applicability. The protein-free medium and the other serum-free formulations tested are able to support long-term growth of hybridoma and myeloma cell lines. Growth periods with various media for individual flasks of several different lines are given in Table IV. The microscopic appearance of cells grown in the protein-free medium (or other serum-free media) for several months is as good as with any other medium tested. However, in the context of preparing monoclonal antibodies, it is not only necessary that good cell growth be obtained, but also that Ig production remains stable.

Figure 2:
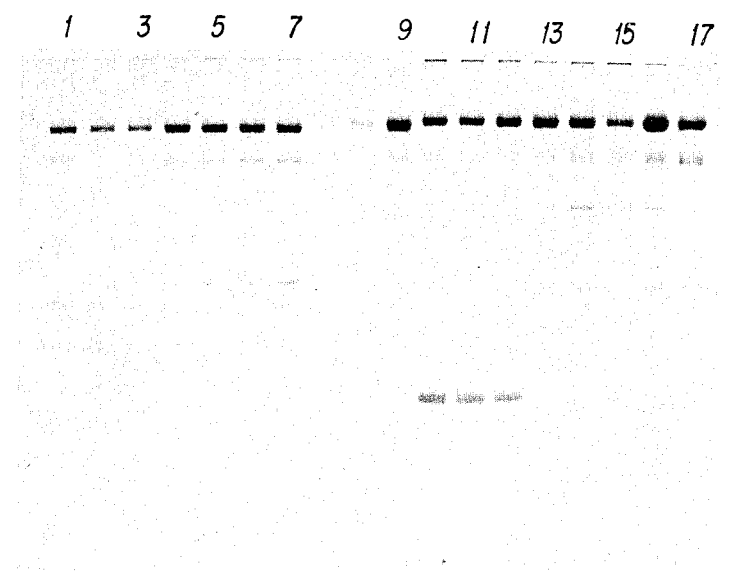
FIG. 2 shows an SDS-PAGE analysis of long term antibody production in a serum-free medium in comparison to a protein-free medium of the invention.

In the case of two lines, Ml/70.15.1 and 456,31, stability of Ig production by the cells in an individual flask was studied for an extended period of time. As indicated in FIG. 2, high levels (about 50–200 μg/ml) of Ig production were maintained for as long as 6 months by lines Ml/70.15.1 and 456,31 when grown for long periods in serum-free and protein-free media. Flask C of line Ml/70.15.1 was started (day zero) from a flask previously maintained in BM+1% FCS. After 5 days, it was fed with BM+½ TEI+TEII +Ins+Tf. After 100 days, it was fed with BM+½ TEI+TEII+Ins. After 108 days, it was fed with BM+ ½ TEI+TEII. Flask C of line 456,31 was started (day zero) from a flask previously maintained in DME+10% horse serum (HS). After 5 days, it was fed with BM+1% FCS. After 9 days, it was fed with BM+½ TEI+Ins+Tf+L. Between days 56 and 65, the medium was gradually switched to BM+½ TEI+TEII. The stability of Ig production is indicated by FIG. 2, which shows an SDS-PAGE analysis of Ig production at various times. Lane 1: Ml/70.15.1 (BM+½ TEI+TEII+Ins+Tf), day 13. Lane 2: Ml/70.15.1, same as above day 32. Lane 3: Ml/70.15.1, same as above, day 65. Lane 4: Ml/70.15.1, same as above, day 89. Lane 5: Ml/70.15.1 (BM+½ TEI+TEII), day 129. Lane 6: Ml/70.15.1, same as above, day 178. Lane 7: Ml/70.15.1, same as above, day 185. Lane 8: purified IgG$_{2b}$ concentration standard 100 μg/ml. Lane 9: 456,31 (BM+½ TEI+Ins+Tf+L), day 12. Lane 10: 456,31, same as above, day 26. Lane 11: 456,31, same as above, day 49. Lane 12: 456,31 (BM+½ TEI+TEII), day 68. Lane 13: 456,31, same as above, day 93. Lane 14: 456, 31, same as above, day 114. Lane 15: 456,31, same as above, day 173. Lane 16: 456,31, same as above, day 223.

Moreover, Ig production was stable and of comparable magnitude, not only for those serum-free formulations in which the basal medium was supplemented with insulin, insulin+transferrin, or insulin+transferrin+liposomes, but also for the protein-free formulation. The flask containing 456,31 cells was fed with protein-free medium for 77 days without any indication of a decline in Ig production. For the flask containing Ml/70.15.1 cells, the period of growth in the protein-free medium was 158 days and good stability was obtained.

Another cell line, Ml/69.16.11, exhibited a gradual decline in Ig production when grown in either BM+½ TEI+Ins+Tf+0.1% FCS or BM+½ TEI+Ins+TF (data not shown). After growth in these media for a period of 6–8 weeks, Ig production declined to levels that were barely detectable by SDS-PAGE. When flasks grown in these media were eventually switched to BM+½ TEI+TEII, Ig production was undetectable. Nonetheless, excellent growth of this line, on the basis of microscopic observation and medium acidification, was obtained with the protein-free medium, as well as with the other serum-free media. Since a parallel comparison of Ig production in serum-free (or 0.1% FCS) and serum (1% or 10%)-supplemented media with this line was not carried out, it is not possible to determine whether the observed instability is an intrinsic property of the line or is a result of the serum-free cultivation conditions.

With regard to the other lines grown in protein-free medium, namely 53-7.313, 53-6.72, 2b-187.1, HO13-4-9 and Hyl, stability of Ig production has not yet been evaluated after extended periods of cultivation. However, in the event that some lines are unstable, the fact that vigorous growth has been obtained suggests that appropriate recloning may facilitate the practical long-term cultivations of these lines in protein-free medium. For example, the Ig non-producing fusion line P3X63-Ag8.653 has been adapted to protein-free cultivation conditions, thereby allowing the production of conditioned medium that is free of both serum proteins and myeloma immunoglobulins. This conditioned medium may be useful for cloning purposes and also as a source of any cell-produced growth factors that may facilitate growth in a protein-free medium. In addition, interferon production by Ehrlich ascites tumor cells has been found to be comparable to interferon production by these cells in serum-supplemented media.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. In a protein-free chemically defined tissue culture medium wherein the improvement comprises a combination of a basal medium and a trace element mixture, said trace element mixture comprising a bromine salt, a fluorine salt, and an iodine salt, and, as metal salt other than positive metal ions selected from Group IA and IIA of the Periodic Table of the Elements, said mixture containing only at least one species selected from each member of the group consisting of copper salts, iron salts, zinc salts, manganese salts, silicon salts, molybdenum salts, vanadium salts, nickel salts, tin salts, aluminum salts, silver salts, barium salts, cadminum salts, cobalt salts, chromium salts, germanium salts, rubidium salts, zirconium salts and selenium salts.

2. The tissue culture medium of claim 1, wherein said trace element mixture produces a solution containing $3.1 \times 10^{-5}$–$3.1 \times 10^{-3}$ mg/L copper, $8.4 \times 10^{-3}$–$8.4 \times 10^{-1}$ mg/L iron, $9.9 \times 10^{-3}$–$9.9 \times 10^{-1}$ mg/L zinc, $2.8 \times 10^{-6}$–$2.8 \times 10^{-4}$ mg/L manganese, $7.0 \times 10^{-4}$–$7.0 \times 10^{-2}$ mg/L silicon, $4.8 \times 10^{-6}$–$4.8 \times 10^{-4}$ mg/L molybdenum, $1.3 \times 10^{-5}$–$1.3 \times 10^{-3}$ mg/L vanadium, $1.4 \times 10^{-6}$–$1.4 \times 10^{-4}$ mg/L nickel, $3.1 \times 10^{-6}$–$3.1 \times 10^{-4}$ mg/L tin, $1.3 \times 10^{-5}$–$1.3 \times 10^{-3}$ mg/L aluminum, $1.1 \times 10^{-5}$–$1.1 \times 10^{-3}$ mg/L silver, $1.4 \times 10^{-4}$–$1.4 \times 10^{-2}$ mg/L barium, $4.0 \times 10^{-6}$–$4.0 \times 10^{-4}$ mg/L bromine, $1.1 \times 10^{-4}$–$1.1 \times 10^{-2}$ mg/L cadmium, $6.0 \times 10^{-5}$–$6.0 \times 10^{-3}$ mg/L cobalt, $5.3 \times 10^{-6}$–$5.3 \times 10^{-4}$ mg/L chromium, $2.3 \times 10^{-4}$–$2.3 \times 10^{-2}$ mg/L fluorine, $3.7 \times 10^{-5}$–$3.7 \times 10^{-3}$ mg/L germanium, $4.1 \times 10^{-6}$–$4.1 \times 10^{-4}$ mg/L iodine, $8.5 \times 10^{-5}$–$8.5 \times 10^{-3}$ mg/L rubidium, $9.0 \times 10^{-5}$–$9.0 \times 10^{-3}$ mg/L zirconium, and $2.6 \times 10^{-4}$–$2.6 \times 10^{-2}$ mg/L selenium when dissolved in said amount of water.

3. The tissue culture medium of claim 1, wherein said trace element mixture produces a solution containing $1.6 \times 10^{-4}$–$6.4 \times 10^{-4}$ mg/L copper, $4.6 \times 10^{-2}$–$1.8 \times 10^{-1}$ mg/L iron, $4.9 \times 10^{-2}$–$1.9 \times 10^{-1}$ mg/L zinc, $1.4 \times 10^{-5}$–$5.6 \times 10^{-5}$ mg/L manganese, $3.5 \times 10^{-3}$–$1.4 \times 10^{-2}$ mg/L silicon, $2.4 \times 10^{-5}$–$1.0 \times 10^{-4}$ mg/L silicon, $2.4 \times 10^{-5}$–$1.0 \times 10^{-4}$ mg/L molybdenum, $6.5 \times 10^{-5}$–$2.6 \times 10^{-4}$ mg/L vanadium, $7.5 \times 10^{-6}$–$3.0 \times 10^{-5}$ mg/L nickel, $1.5 \times 10^{-5}$–$6.0 \times 10^{-5}$ mg/L tin, $6.5 \times 10^{-5}$–$2.6 \times 10^{-4}$ mg/L aluminum, $5.0 \times 10^{-5}$–$2.2 \times 10^{-4}$ mg/L silver, $7.0 \times 10^{-4}$–$2.8 \times 10^{-5}$ mg/L barium, $2.0 \times 10^{-5}$–$8.0 \times 10^{-5}$ mg/L bromine, $5.5 \times 10^{-4}$–$2.2 \times 10^{-3}$ mg/L cadminum, $3.0 \times 10^{-4}$–$1.2 \times 10^{-3}$ mg/L cobalt, $2.5 \times 10^{-5}$–$1.1 \times 10^{-4}$ mg/L chromium, $1.2 \times 10^{-3}$–$4.6 \times 10^{-3}$ mg/L fluorine, $1.8 \times 10^{-4}$–$7.4 \times 10^{-4}$ mg/L germanium, $2.0 \times 10^{-5}$–$8.2 \times 10^{-5}$ mg/L iodine, $4.2 \times 10^{-4}$–$1.7 \times 10^{-3}$ mg/L rubidium, $4.5 \times 10^{-4}$–$1.8 \times 10^{-3}$ mg/l zirconium, and $1.3 \times 10^{-3}$–$5.1 \times 10^{-3}$ mg/L selenium when dissolved in said amount of water.

4. The tissue culture medium of claim 1, wherein said basal culture medium is capable of supporting long term growth of a hybridoma cell line without said trace element mixture when supplemented with 5% fetal calf serum.

5. The tissue culture medium of claim 1, wherein said basal medium contains an amino acid, an inorganic salt, a vitamin, an antibotic, a fatty acid, an amine, a sulfur source, or a non-proteinaceous growth providing hormone.

6. The tissue culture medium of claim 5, wherein said tissue culture medium contains a component selected from the group consisting of L-alanine, minimum concentration 0.2 mg/L; L-arginine, minimum concentration 1.5 mg/L; L-asparagine, minimum concentration 0.2 mg/L; L-aspartic acid, minimum concentration 0.2 mg/L; L-cystine, minimum concentration 0.1 mg/L; L-cysteine, minimum concentration 0.5 mg/L; L-glumatic acid, minimum concentration 0.4 mg/L; L-glutamine, minimum concentration 3.7 mg/L; glycine, minimum concentration 0.1 mg/L; L-histidine, minimum concentration 0.3 mg/L; L-isoleucine, minimum concentration 0.5 mg/L; L-leucine, minimum concentration 0.6 mg/L; L-lysine, minimum concentration 0.9 mg/L; L-methionine, minimum concentration 0.2 mg/L; L-phenylalanine, minimum concentration 0.4 mg/L; L-proline; minimum concentration 0.4 mg/L; :L-serrine, minimum concentration 0.3 mg/L; L-threonine, minimum concentration 0.5 mg/L; L-tryptophan, minimum concentration 0.09 mg/L; L-tyrosine, minimum concentration 0.5 mg/L; and L-valine, minimum concentration 0.5 mg/L, when dissolved in said amount of water.

7. The tissue culture medium of claim 5, wherein said tissue culture medium contains a component selected from the group consisting of 1.7–170 mg/L L-alanine, 14.7–1470 mg/L L-arginine, 2.0–200 mg/L-asparagine, 2.2–220 mg/L L-aspartic acid, 1.1–110 mg/L L-cystine, 4.9–490 mg/L L-cysteine, 4.5–450 mg/L L-glutamic acid, 36.5–3650 mg/L L-glutamine, 1.1–110 mg/L glycine, 3.2–320 mg/L L-histidine, 5.4–540 mg/ L L-isoleucine, 5.9–590 mg/L L-leucine, 9.1–910 mg/L L-lysine, 1.7–170 mg/L L-methionine, 3.5–350 mg/L L-phenylalanine 3.7–370 mg/L L-proline, 2.6–260 mg/L L-serine, 5.3–530 mg/L L-threonine, 0.9–90 mg/ L L-tryptophan, 5.2–520 mg/L L-tyrosine, and 5.3–530 mg/L L-valine, when dissolved in said amount of water.

8. The tissue culture medium of claim 5, wherein said tissue culture medium contains a component selected from the group consisting of 8.5–34 mg/L L-alanine, 74–295 mg/L L-arginine, 10–40 mg/L L-asparagine, 11–43 mg/L L-aspartic acid, 5.5–22 mg/L L-cystine, 25–98 mg/L L-cysteine, 22–90 mg/L L-glutamic acid, 192–730 mg/L L-glutamine, 5.5–23 mg/L glycine, 16–63 mg/L L-histidine, 27–109 mg/L L-isoleucine, 29–118 mg/L L-leucine, 46–183 mg/L L-lysine, 8.5–34 mg/L L-methionine, 18–71 mg/L L-phenylalanine, 19–75 mg/L L-proline, 13–53 mg/L L-serine, 27–106 mg/L L-threonine, 4.5–18 mg/L L-tryptophan, 26–104 mg/L L-tyrosine, and 26–106 mg/L L-valine, when dissolved in said amount of water.

9. The tissue culture medium of claim 5, wherein said tissue culture medium contains a component selected from the group consisting of 0.36–3600 mg/L $Ca^{2+}$, 1.76–17,300 mg/L $K^+$, 0.17–1720 mg/L $Mg^{2+}$, 30–$\times 10^5$ mg/L $Na^+$, 39–$3.9 \times 10^5$ mg/L $Cl^-$, 0.96–10,000 mg/L $PO_4^{3-}$, and 15–$1.5 \times 10^5$ mg/L $HCO_3^-$, when dissolved in said amount of water.

10. The tissue culture medium of claim 5, wherein said tissue culture medium contains a component selected from the group consisting of 9.0–1.44 mg/L $Ca^{2+}$, 43–690 mg/L $K^+$, 4.3–69 mg/L $Mg^{2+}$, 750–12,000 mg/L $Na^+$, 975–15,600 mg/L $CL^-$, 24–400 mg/L $PO_4^{3-}$, and 380–6100 mg/L $HCO_3^-$, when dissolved in said amount of water.

11. The tissue culture medium of claim 5, wherein said tissue culture medium contains a component selected from the group consisting of 18–72 mg/L $Ca^{2+}$, 86–345 mg/L $K^+$, 8.6–35 mg/L $Mg^{2+}$, 1500–6000 mg/L $Na^+$, 1950–7800 mg/L $Cl^-$, 48–192 mg/L $PO_4^{3-}$, and 760–3050 mg/L $HCO_3$, when dissolved in said amount of water.

12. The tissue culture medium of claim 5, wherein said tissue culture medium contains a component selected from the group consisting of $1.0 \times 10^{-4}$–1.0 mg/L biotin, 0.022–225 mg/L pantothenate, 0.090–900 mg/L choline, 0.027–275 mg/L folic acid, 0.12–1250 mg/L inositol, 0.020–200 mg/L nicotinamide, 0.020–200 mg/L pyridoxal, $3.1 \times 10^{-4}$–3.1 mg/L pyridoxine, $2.2 \times 10^{-3}$–22 mg/L riboflavin, 0.022–220 mg/L thiamine, $6.9 \times 10^{-3}$–69 mg/L vitamin $B_{12}$, 1.1–11,000 mg/L pyruvate, 14–$1.4 \times 10^5$ mg/L glucose, 0.1–1000 mg/L phenol red, $8.1 \times 10^{-4}$–8.1 mg/L putrescine, 0.020–200 mg/L hypoxanthine, $4.1 \times 10^{-4}$–4.1 mg/L linoleic acid, $1.0 \times 10^{-3}$–12 mg/L lipoic acid, $3.6 \times 10^{-3}$–37 mg/L thymidine, 1–10,000 U/ml penicillin, 1–10,000 μg/ml streptomycin, 0.063–625 μL/L α-thioglycerol, and $1.0 \times 10^{-4}$–1.0 mg/L progesterone, when dissolved in said amount of water.

13. The tissue culture medium of claim 5, wherein said tissue culture medium contains a component selected from the group consisting of $2.5 \times 10^{-3}$–0.040 mg/L biotin, 0.56–9.0 mg/L pantothenate, 2.3–36 mg/L choline, 0.66–10.6 mg/L folic acid, 3.1–50 mg/L inositol, 0.50–8.0 mg/L nicotinamide, 0.50–8.0 mg/L pyridoxal, $7.8 \times 10^{-3}$–0.12 mg/L pyridoxal, $7.8 \times 10^{-3}$–0.12 mg/L pyridoxine, 0.055–0.88 mg/L riboflavin, 0.55–8.8 mg/L thiamine, 0.17–2.7 mg/L vitamin $B_{12}$, 28–450 mg/L pyruvate, 350–5600 mg/L glucose, 2.6–43 mg/L phenol red, 0.020–0.32 mg/L putrescine, 0.50–8.0 mg/L hypoxanthine, 0.010–0.16 mg/L linoleic acid, 0.025–0.40 mg/L lipoic acid, 0.091–1.5 mg/L thymidine, 25–400 U/ml penicillin, 25–400 μg/ml streptomycin, 1.6–25 μL/L α-thioglycerol, and $2.5 \times 10^{-3}$–0.040 mg/L progesterone, when dissolved in said amount of water.

14. The tissue culture medium of claim 5, wherein said tissue culture medium contains a component selected from the group consisting of $5.0 \times 10^{-3}$–0.020 mg/L biotin, 1.1–4.5 mg/L pantothenate, 4.6–18 mg/L choline, 1.3–5.3 mg/L folic acid, 6.2–25 mg/L inositol, 1.0–4.0 mg/L nicotinamide, 1.0–4.0 mg/L pyridotal, 0.015–0.0060 mg/L pyridoxine, 0.11–0.44 mg/L riboflavin, 1.1–4.4 mg/L thiamine, 0.34–1.4 mg/L vitamin $B_{12}$, 56–225 mg/L pyruvate, 700–6300 mg/L glucose, 5.2–22 mg/L phenol red, 0.040–0.16 mg/L putrescine, 1.0–4.0 mg/L hypoxanthine, 0.020–0.080 mg/L linoleic acid, 0.050–0.20 mg/L lipoic acid, 0.18–0.75 mg/L thymidine, 50–200 U/ml penicillin, 50–200 μg/ml streptomycin, 3.2–13 μL/L α-thioglycerol, and $5.0\times10^{-3}$–0.020 mg/L progesterone, when dissolved in said amount of water.

15. The tissue culture medium of claim 1, comprising a buffering agent.

16. The tissue culture medium of claim 1, wherein said basal medium has a pH of from 6.5 to 8.2.

17. In a method of cultivating hybridoma cells in a protein free basal medium, the improvement comprising adding to the basal medium a trace element mixture consisting essentially of copper, iron, zinc, manganese, silicon, molybdenum, banadium, nickel, tin, aluminum, silver, barium, bromine, cadmium, cobalt, chromium, fluorine, germanium, iodine, rubidium, ziroconium, and selenium.

18. The method of claim 17 wherein the basal medium contains 8.5 to 34 mg/L L-alanine, 74 to 295 mg/L L-arginine, 10 to 40 mg/L L-asparagine, 11 to 43 mg/L L-aspartic acid, 5.5 to 22 mg/L L-cystine, 24 to 98 mg/L L-cysteine, 22 to 90 mg/L L-glutamic acid, 192 to 730 mg/L L-glutamine, 5.5 to 23 mg/L glycine, 16 to 63 mg/L L-histidine, 27 to 109 mg/L L-isoleucine, 29 to 118 mg/L L-leucine, 46 to 183 mg/L L-lysine, 8.5 to 34 mg/L L-methionine, 18 to 71 mg/L L-phenylalanine, 19 to 75 mg/L L-proline, 13 to 53 mg/L L-serine, 27 to 106 mg/L L-threonine, 4.5 to 18 mg/L L-tryptophan, 26 to 104 mg/L L-tyrosine, and 26 to 106 mg/L valine.

19. The method of claim 18, wherein the basal medium contains 18 to 72 mg/L $Ca^{2+}$, 86 to 345 mg/L $K^+$, 8.6 to 35 mg/L $Mg^{2+}$, 1500 to 6000 mg/L $Na^+$, 1950 to 7800 mg/L $Cl^-$, 48 to 192 mg/L $PO_4^{3-}$, and 760 to 3050 mg/L $HCO_3^-$.

20. The method of claim 18, wherein the basal medium contains $5.0\times10^{-3}$ to 0.020 mg/L biotin, 1.1 to 4.5 mg/L of pantothenate, 4.6 to 18 mg/L of choline, 1.3 to 5.3 mg/L of folic acid, 6.2 to 25 mg/L of inositol, 1.0 to 4.0 mg/L of nicotinamide, 1.0 to 4.0 mg/L of pyridoxal, 0.015 to 0.060 mg/L of pyridoxine, 0.11 to 0.44 mg/L of riboflavin, 1.1 to 4.4 mg/L of thiamine, 0.34 to 1.4 mg/L of vitamin $B_{12}$, 56 to 225 mg/L of pyruvate, 700 to 6300 mg/L of glucose, 5.2 to 22 mg/L of phenol red, 0.040 to 0.16 mg/L of putrescine, 1.0 to 4.0 mg/L of hypoxanthine, 0.020 to 0.080 mg/L of linoleic acid, 0.050 to 0.20 mg/L of lipoic acid, 0.18 to 0.75 mg/L of thymidine, 50 to 200 U/ml of penicillin, 50 to 200 μg/ml of streptomycin, 3.2 to 13 μL/L of α-thioglycerol, and $5.0\times10^{-3}$ to 0.020 mg/L of progesterone.

21. The method of claim 18, comprising:
contacting the said cells with a medium containing $5.0\times10^{-3}$ to 0.0020 mg/L biotin; 1.1 to 4.5 mg/L of pentothenate; 4.6 to 18 mg/L of choline; 1.3 to 5.3 mg/L of folic acid; 6.2 to 25 mg/L of inositol; 1.0 to 4.0 mg/L of nicotinamide; 1.0 to 4.0 mg/L of pyridoxal; 0.015 to 0.060 mg/L of pyridoxine; 0.11 to 0.44 mg/L of riboflavin; 1.1 to 4.4 mg/L of thiamine; 0.34 to 1.4 mg/L of vitamine $B_{12}$; 56 to 225 mg/L of pyruvate; 700 to 6300 mg/L of glucose; 5.2 to 22 mg/L of phenol red; 0.040 to 0.16 mg/L of putrescine; 1.0 to 4.0 mg/L of hypoxanthine; 0.020 to 0.080 mg/L of linoleic acid; 0.050 to 0.20 mg/L of lipoic acid; 0.18 to 0.75 mg/L of thymidine; 50 to 200 U/ml of penicillin; 50 to 200 g/ml of streptomycin; 3.2 to 13 L/L of a-thioglycerol; $5.0\times10^{-3}$ to 0.020 mg/L of progesterone; 18 to 72 mg/L $Ca^{2+}$; 86 to 345 mg/L $K^+$; 8.6 to 35 mg/L $Mg^{2+}$; 500 to 6000 mg/L $Na^+$; 1950 to 7800 mg/L $Cl^-$; 48 to 192 mg/L $PO_4^{3-}$; and 760 to 3050 mg/L $HCO_3^-$;
and growing the said cells.

22. The method of claim 17 wherein the basal medium contains 18 to 72 mg/L $Ca^{2+}$, 86 to 345 mg/L $K^+$, 8.6 to 35 mg/L $Mg^{2+}$, 1500 to 6000 mg/L $Na^+$, 1950 to 7800 mg/L $Cl^-$, 48 to 192 mg/L $PO_4^{3-}$, and 760 to 3050 mg/L $HCO_3^-$.

23. The method of claim 17, wherein the basal medium contains $5.0\times10^{-3}$ to 0.020 mg/L biotin, 1.1 to 4.5 mg/L of pantothenate, 4.6 to 18 mg/L of choline, 1.3 to 5.3 mg/L of folic acid, 6.2 to 25 mg/L of inositol, 1.0 to 4.0 mg/L of nicotinamide, 1.0 to 4.0 mg/L of pyridoxal, 0.015 to 0.060 mg/L of pyridoxine, 0.11 to 0.44% mg/L of riboflavin, 1.1 to 4.4 mg/L of thiamine, 0.34 to 1.4 mg/L of vitamin $B_{12}$, 56 to 225 mg/L of pyruvate, 700 to 6300 mg/L of glucose, 5.2 to 22 mg/L of phenol red, 0.040 to 0.16 mg/L of putrescine, 1.0 to 4.0 mg/L of hypoxanthine, 0.020 to 0.080 mg/L of linoleic acid, 0.050 to 0.20 mg/L of lipoic acid, 0.18 to 0.75 mg/L of thymidine, 50 to 200 U/ml of penicillin, 50 to 200 μg/ml of streptomycin, 3.2 to 13 μL/L of α-thioglycerol, and $5.0\times10^{-3}$ to 0.020 mg/L of progesterone.

* * * * *